United States Patent [19]
Fiedler

[11] Patent Number: 5,830,951
[45] Date of Patent: Nov. 3, 1998

[54] POLYVINYLSILOXANE IMPRESSION MATERIAL

[75] Inventor: Jurgen Hans Fiedler, Constance, Germany

[73] Assignee: Dentsply DeTrey G.m.b.H., Dreieich, Germany

[21] Appl. No.: 767,134

[22] Filed: Dec. 19, 1996

Related U.S. Application Data

[63] Continuation-in-part of Ser. No. 490,690, Apr. 13, 1995, Pat. No. 5,661,222.

[51] Int. Cl.$^6$ .................................................... C08K 3/36
[52] U.S. Cl. ..................... 525/478; 524/588; 524/493; 106/35; 106/38.22; 264/16; 433/214; 523/109; 528/15; 528/31; 528/32; 528/39
[58] Field of Search .......................... 525/478; 524/538, 524/493; 264/16; 106/38.22, 35; 433/214; 528/15, 31, 32, 39; 523/109

[56] References Cited

U.S. PATENT DOCUMENTS

| | | | |
|---|---|---|---|
| 2,676,182 | 9/1954 | Daubt et al. | 260/448.2 |
| 2,857,356 | 10/1958 | Goodwin . | |
| 3,093,133 | 6/1963 | Evertt | 128/216 |
| 3,419,593 | 12/1968 | Willing | 260/448.2 |
| 3,527,659 | 9/1970 | Keil | 117/145 |
| 3,715,334 | 2/1973 | Karstedt | 260/46.5 |
| 3,775,452 | 11/1973 | Karstedt | 260/429 |
| 3,950,300 | 4/1976 | Hittmair et al. | 260/37 SB |
| 3,957,683 | 5/1976 | Hitmair et al. | 252/428 |
| 4,035,453 | 7/1977 | Hittmair et al. | 264/16 |
| 4,222,983 | 9/1980 | August et al. | 264/220 |
| 4,248,750 | 2/1981 | Murakami et al. | 260/29.1 |
| 4,276,252 | 6/1981 | Kreis et al. | 264/222 |
| 4,288,345 | 9/1981 | Ashby et al. | 252/431 |
| 4,340,709 | 7/1982 | Jeram et al. | 528/15 |
| 4,359,565 | 11/1982 | Puppe et al. | 528/15 |
| 4,387,240 | 6/1983 | Berg | 556/440 |
| 4,424,328 | 1/1984 | Ellis | 526/279 |
| 4,535,141 | 8/1985 | Kroupa | 528/15 |
| 4,568,707 | 2/1986 | Voigt et al. | 523/109 |
| 4,575,545 | 3/1986 | Nakos et al. | 526/242 |
| 4,593,084 | 6/1986 | Chandra et al. | 528/15 |
| 4,600,731 | 7/1986 | Louis et al. | 523/109 |
| 4,609,687 | 9/1986 | Schwabe et al. | 523/109 |
| 4,657,959 | 4/1987 | Bryan et al. | 524/266 |
| 4,687,870 | 8/1987 | Cavezzan et al. | 556/136 |
| 4,691,039 | 9/1987 | Aasen et al. | 556/446 |
| 4,719,273 | 1/1988 | Seyferth et al. | 528/15 |
| 4,722,968 | 2/1988 | Shimizu et al. | 524/862 |
| 4,741,966 | 5/1988 | Cavezzan et al. | 428/447 |
| 4,752,633 | 6/1988 | Aasen et al. | 524/266 |
| 4,772,515 | 9/1988 | Hara et al. | 428/447 |
| 4,776,704 | 10/1988 | Kopunek et al. | 366/184 |
| 4,782,101 | 11/1988 | Waller et al. | 523/120 |
| 4,806,575 | 2/1989 | Waller et al. | 523/120 |
| 4,806,592 | 2/1989 | Saruyama | 524/860 |
| 4,836,853 | 6/1989 | Gribi | 106/35 |
| 4,845,164 | 7/1989 | Gutek | 528/15 |
| 4,849,491 | 7/1989 | Ogawa et al. | 528/15 |
| 4,882,398 | 11/1989 | Mbah | 525/478 |
| 4,906,446 | 3/1990 | Engelbrecht et al. | 423/335 |
| 4,916,169 | 4/1990 | Boardman et al. | 522/27 |
| 4,957,667 | 9/1990 | Hamer | 264/16 |
| 4,965,295 | 10/1990 | Schwabe et al. | 523/109 |
| 4,966,934 | 10/1990 | Huang et al. | 524/315 |
| 5,004,792 | 4/1991 | Maxson | 528/15 |
| 5,064,891 | 11/1991 | Fujiki et al. | 524/264 |
| 5,085,811 | 2/1992 | Hamer | 264/16 |
| 5,145,933 | 9/1992 | Grisoni et al. | 528/15 |
| 5,169,919 | 12/1992 | Terae et al. | 528/15 |
| 5,239,035 | 8/1993 | Maxson | 528/115 |
| 5,288,830 | 2/1994 | Itou et al. | 528/15 |
| 5,306,797 | 4/1994 | Ikeno | 528/15 |
| 5,331,075 | 7/1994 | Sumpter et al. | 528/15 |
| 5,367,001 | 11/1994 | Itoh et al. | 523/109 |
| 5,371,162 | 12/1994 | Konings et al. | 528/15 |
| 5,403,885 | 4/1995 | Voigt et al. | 524/731 |
| 5,484,871 | 1/1996 | Stepp | 528/31 |
| 5,555,584 | 9/1996 | Moore, III et al. | 12/142 N |
| 5,580,921 | 12/1996 | Stepp et al. | 524/731 |

FOREIGN PATENT DOCUMENTS

| | | |
|---|---|---|
| 152 887 | 2/1985 | European Pat. Off. . |
| 231 420 | 8/1987 | European Pat. Off. . |
| 268 347 | 5/1988 | European Pat. Off. . |
| 480 238 | 4/1992 | European Pat. Off. . |
| 522 341 | 1/1993 | European Pat. Off. . |
| 614 655 | 4/1994 | European Pat. Off. . |
| 602 128 | 12/1995 | European Pat. Off. . |
| 41 29 613 | 3/1993 | Germany . |
| 2 292 153 | 2/1996 | United Kingdom . |
| 93/04659 | 3/1993 | WIPO . |
| 93/17654 | 9/1993 | WIPO . |

OTHER PUBLICATIONS

Rheological Properties of Elastomers during Setting–J.F. McCabr and T.E. Carrick, Aug. 1989.

*Primary Examiner*—Margaret W. Glass
*Attorney, Agent, or Firm*—Douglas J. Hura; James B. Bieber

[57] ABSTRACT

Improved two component polymerizable polyorganosiloxane compositions are described, particularly for use in making dental impressions, having improved tear strength and wettability. Improved tear strength results from inclusion of a quadri-functional polysiloxane having a vinyl content of 0.16 to 0.24 m-mole/g. Working time is maintained by including sufficient amounts of a retarder composition that delays onset of the vinyl polymerization. Wettability is improved by including a surfactant resulting in a surface contact angle with water at three minutes of less than 50°. The surfactant chosen has an HLB of 8–11, such that the wetting contact angle is achieved within less than two minutes and remains wetting throughout the working time of the impression taking, substantially improving impression quality. A low viscosity impression material is provided and includes a base component and a catalyst component. Both components are siloxane-based materials.

3 Claims, 4 Drawing Sheets

POLYVINYLSILOXANE IMPRESSION MATERIAL

This is a Continuation-in-Part of U.S. Pat. application Ser. No. 08/490,690, filed Apr. 13, 1995, now U.S. Pat. No. 5,661,222.

BACKGROUND OF THE INVENTION

This invention is directed to improvements in room temperature polymerizable polyorganosiloxanes having good dimensional stability upon curing or hardening and having improved flow characteristics. More particularly, this invention is directed to improvements in compositions that are generally of the type comprising two components, one component comprising organopolysiloxanes having vinyl groups, capable of undergoing addition reactions with organopolysiloxanes having silicone-bonded hydrogen atoms. The second component comprises a catalyst capable of promoting the addition of hydrogen atoms bonded to silicone atoms across the vinyl groups. In one embodiment, the inventive material has a high tear strength, low viscosity and is highly hydrophilic.

A major field for the use of certain of these room temperature curable polyorganosiloxane compositions is dentistry. Such materials are typically employed as impression materials for securing an analog representation of oral hard and soft tissue to support subsequent elaboration of crowns, bridges, dentures and other oral prostheses. For dental use, extraordinary fidelity of structural reproduction is required in order to ensure good fidelity of oral prosthetic fit and the like. In this regard, changes in the dimensions of the impression material during curing are to be avoided. Moreover, the surface of the reproductions or oral prosthetics and the like must be exceptionally free from irregularities, blemishes, pits, and other imperfections. This is so because castings and prostheses derived from such impressions must have good surface qualities and be free from pits and irregularities in order to have proper fit, to achieve good adhesion, and to avoid irritation of sensitive mouth structures. These polyorganosiloxanes will also be useful in other fields where detailed reproductions are important such as in the science of metrology, laboratory processing of SEM and even jewelry fabrication and the like.

In employing polyorganosiloxanes as dental impression materials, a number of difficulties have arisen. First of all, tear strength tends to be low. It is necessary, in effectively taking an impression, to be able to easily remove the impression, from the dentition without tearing, particularly at thin marginal areas, to preserve fine detail. In the past, fillers of various types have been added to improve tear strength. Such additions may result in some improvement, on the order of about 10%, but such improvements have proved inadequate.

Paradiso in WO 93/17654 describes improving tear strength by incorporating multi-functional, including quadri-functional, polysiloxane components into the impression material, to add increased cross-linking to the resulting cured impression material matrix, particularly along the length of the linear vinyl end-stopped polysiloxane principal component. The Paradiso composition comprises SiOH groups capped off with $Me_3Si$ units that form pendants from the molecule. These pendants provide only mechanical or physical interlinking between the linear polysiloxane chains. This solution is deficient, being non-chemical and low in cross-linking density.

Voigt et al in EP 0 522 341 Al describes very short processing times of 35–45 seconds for forming dentition bite registration devices, utilizing a "QM" resin as a means of speeding and increasing cross-linking. These resins comprise as Q, the quadri-functional $SiO_{4/2}$ and as M, building blocks such as monofunctional units $R_3SiO_{1/2}$ wherein R is vinyl, methyl, ethyl or phenyl, or similar tri or bi-functional units. voigt notes that an elastomer with small elastic deformation having a higher tenacity and hardness results. However, such material lacks flexibility, having a low strain value, and is unsuitable for impression taking. The increased cross-linking rate of the QM resin also results in very limited processing times that are unsatisfactory.

The other major, well-known difficulties with polyorganosiloxane impression materials are caused by its inherent hydrophobic character. Such characteristics make reproduction of hard and soft oral tissue difficult since the oral cavity environment is wet and often contaminated with saliva or blood. The hydrophobicity of the impression material can result in loss of surface detail often at critical surfaces of the dentition.

A number of improvements of polyorganosiloxane impression materials focus upon adding a surfactant component to the dental impression material in order to reduce the hydrophobic nature of the polysiloxanes and make the composition more hydrophilic. Thus, Bryan et al in U.S. Pat. No. 4,657,959 describes adding an ethoxylated nonionic surface active agent containing siloxane or perfluoroalkyl solubilizing groups to achieve a three minute water contact angle below about 65°. While surfactants including hydrocarbyl groups, for rendering the surfactant soluble or dispersible in silicone prepolymer, are mentioned, including ethyleneoxy groups, the results achieved appeared to be less than optimal.

As stated above, all silicone material are known to have highly hydrophobic properties. Therefore, these materials are usually not able to wet the surface of the teeth properly, especially under moist conditions. Hydrophilic properties can be achieved in a silicone with the addition of dipoler surfactants. These additives are usually not soluble in the silicone matrix, but rather form an emulsion together with the silicon system. The Theological properties of such materials are characterized by a typical non-Newtonian flow behavior with a high yield stress and a highly sheer stress-dependent viscosity. Non-dipolar surfactants include for example, polyether modified silicones, and do not build proper micelles. The resulting emulsions are therefore not stable and tend to separate. However, the resulting multiple phase systems have a high yield stress which avoids the flow on the tooth surface when no or low stress is applied. Hydrophilic silicones therefore usually have poor flow characteristics under low stress.

Conventional "light bodies" formed from a two component system are usually applied in one of two forms. The first is a handmixed form in the case when the two components have to be mixed by hand. Second is an automixed form when the two components have to be released through a static mixer out of a cartridge. In both cases, the mixablility of the two components are strongly influenced by the rheological properties of the individual components making up the light body. Especially in the most common automixed form, the force to release the material out of the cartridge is influenced by the yield stress of the pastes.

Because of the Theological sub-structures, most conventional hydrophilic silicones have high yield stresses. To take advantage of low forces for releasing the material, large static mixers have to be employed. This leads to a high rate of waste because much of the material often remains in the mixer. Therefore, it is desired to achieve a low yield stress of both the single paste component and the mix in order to minimize the force which is necessary to remove the paste from the cartridge.

With conventional light body formulations a high stress has to be applied to obtain a flow of the impression material into the sulcus and into the other details of the preparation. Low viscosity type materials ("light bodies") are therefore always used in combination with a high viscosity type material in the so called "putty/wash" technique or in the "double mix" technique. To improve the mixablility of the putties, the viscosity of these products must be low. Even in the case where machine mixed heavy bodies are used the stress for releasing is limited by the technical properties of the machine. Higher viscosities lead to longer release times. In cases where these so-called soft putties or heavy bodies are used together with low viscosity silicones, the high yield stress and the highly stressed viscosity of the light body causes problem because it is impossible to generate sufficient pressure by the unset soft putty or heavy body during the taking of the impression. Therefore, a flow into the details of the preparation is not guaranteed. This problem is even more evident when the low viscosity material has a high yield stress.

In addition, the hydrophilic components to improve the wetting properties of the silicone tend to create a new problem. This problem is a stability problem of the cross linking SiH-components against moisture because these functional groups are sensitive against hydrolysis reactions especially under basic conditions. Therefore, it is a preferred embodiment of the present invention to add a water absorbing inorganic filler such as calcium sulfate hemihydrate, anhydrous calcium sulfate, calcium cloride, and the like and adsorbing compounds such as zeoliths, molecular sieves and other similar adsorbing and absorbing compounds.

It is known in the art that a low viscosity can be obtained by the use of a short chain dimethylvinylsiyl terminated polydimethylsiloxane in combination with either a low filler content or no filler at all. These materials usually have a very low mechanical strength such as a low tear strength making them too weak for use as a dental impression material. In cases where the viscosity is too low, the material tends to drop from the teeth and the fillers separate after certain periods of time.

In sum, polyorganosiloxane impression materials still need improvement in viscosity, tear strength and wettability in order to provide improved use of these compositions for taking impressions of oral hard and soft tissues such that adequate working time, tear strength and wettability are provided.

SUMMARY OF THE INVENTION

The new polyvinylsiloxane impression materials are useful in low and high viscosity impression compositions to record hard and soft tissues in the mouth. The new impression material is a platinum-catalyzed, vinylpoly-siloxane material, preferably a two component polymerizable organosiloxane composition, one component including a catalyst for polymerization, comprising:

(a) a QM resin, containing vinyl groups;
(b) a linear vinyl terminated polydimethylsiloxane fluid, forming with said QM resin a dispersion having a vinyl content of about 0.16 to 0.24 m-mole/g;
(c) an organohydrogen polysiloxane for cross-linking said vinyl groups;
(d) an organoplatinum catalyst complex for accelerating polymerization of said components;
(e) a retarder component in sufficient amount for temporarily delaying the onset of said polymerization;
(f) a filler; and
(g) a surfactant that imparts wettability to said composition, wherein said composition surface contact angle with water is less than 50° after three minutes.

Preferably, the dispersion of (a) and (b) has a viscosity of about 5,000–60,000 cps. The dispersion of (a) and (b) may comprise a plurality of dispersion components having desired viscosities and QM resin contents. Preferably, the QM resin-containing dispersions comprise a first dispersion component having a viscosity of about 5,000–7,000 cps and a second dispersion component having a viscosity of about 45,000–60,000 cps, said QM resin comprising about 20–25 weight % of each dispersion.

A preferred QM resin comprises a polyorganosiloxane comprising units of $SiO_{4/2}$ and units of $R^1R^2{}_2SiO_{1/2}$ wherein $R^1$ is unsaturated, preferably vinyl and $R_2$ is alkyl, aryl, etc., such as methyl, ethyl, phenyl, etc. More preferably, the QM resin comprises the formula:

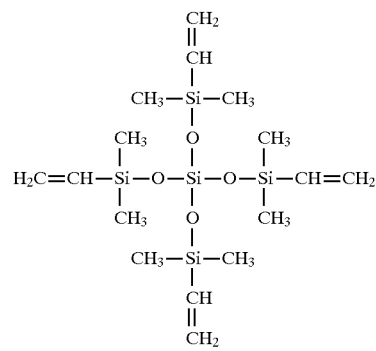

The retarder component of the composition is a low molecular weight, vinyl functional fluid that is a linear or cyclic polysiloxane in an amount of at least about 0.030 weight percent of said composition. Preferably, the retarder component comprises: a fluid 1,3-divinyl, tetramethyldisiloxane, in an amount of about 0.030 to 0.12 weight percent of said composition.

The filler component of the invention comprises about 15 to about 45 weight percent of said composition and preferably includes a filler mixture of about 20 to about 40 weight percent.

A key component of the composition of the invention is the surfactant for imparting wettability, preferably comprising an HLB of about 8–11 and a pH of about 6–8. A most preferred surfactant is a nonionic surfactant, nonylphenoxy poly(ethyleneoxy) ethanol having an HLB of about 10.8.

For compositions of the invention of relatively high viscosity, the composition includes an emulsifying plasticizer that imparts desired handling and flow properties to the catalyst complex, to match those of the second component, wherein a suitable composition for taking a dental impression may conveniently be formed. Preferably, the plasticizer comprises an alkylphthalate at about 0.5 to 2.0% by weight of said catalyst component and is, most preferably, octyl benzyl phthalate.

After polymerization, the compositions of the invention include a tear strength of 270–300 PSI (1.86–2.06 MPa) and a contact angle with water of less than about 50° at three minutes. For the lower viscosity impression material of the invention, tear strength will be somewhat lower at about 200 PSI (1.38 MPa) which is still substantially improved over the prior art.

DESCRIPTION OF THE PREFERRED EMBODIMENTS

Figure 1:
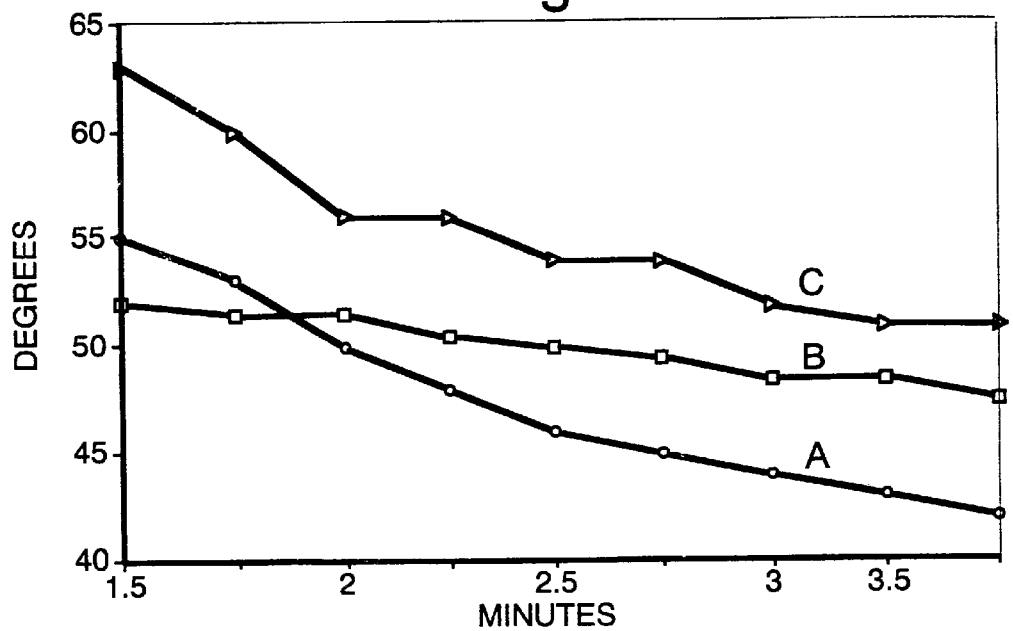
FIG. 1 is a graph showing Wetting Contact Angle, in degrees, as a function of Time, in minutes.

The polymerizable polysiloxane compositions of the instant invention comprise, in general: an organopolysiloxane having at least about two vinyl groups per molecule, further including, dispersed therein, a quadri-functional vinyl polysiloxane resin; an organohydrogen-polysiloxane having at least about two hydrogen atoms bonded to at least two silicone atoms per molecule; a catalyst for accelerating the addition of the silicone atoms bonded to the hydrogen atoms to the polysiloxane vinyl groups; a filler; a low molecular weight retarder composition for delaying onset of polymerization; and an emulsifying surfactant that imparts wettability to said impression material.

The composition of the invention is preferably divided into two components. A first component, which is conveniently referred to as a "Base Paste", contains the vinylorganopolysiloxanes dispersion, the organo-hydrogen-polysiloxane, a portion of the filler and the surfactant. The second component of this two-part composition is referred to as a "Catalyst Paste" and comprises a second portion of the vinyl polysiloxanes, together with the catalyst for accelerating the addition reaction, a scavenging agent for hydrogen released during polymerization and usually, additional quantities of fillers and pigments. Where high viscosity impression materials are desired, an emulsifying plasticizer may be added to the catalyst paste component such that the working viscosities of its two components are compatible and have desired flow characteristics.

A wide variety of organopolysiloxanes having at least about two vinyl groups per molecule are known for inclusion in the dental polysiloxane compositions of the invention to form the dispersion including a quadri-functional vinyl polysiloxane. Each of these materials may be included in greater or lesser degree in accordance with the practice of the instant invention. Preferred for use herein are linear vinyl terminated polydivinylsiloxanes preferably a divinyl polydimethylsiloxane. Such polymers are sold having varying average molecular weights with concomitant variations in viscosity. It is preferred that these materials be selected to have a viscosity appropriate for the conditions to be experienced by the resulting silicone material.

The dispersions of interest have a viscosity range of 5,000–60,000 cps. In practice, it is convenient to employ a blend of the dispersing polymers having differing viscosities and physical properties to provide compositions having a desired thixotropicity and viscosity.

The dispersions of interest are preferably formed in two viscosity ranges: (1) a first dispersion having a viscosity of about 5000–7000 cps; and (2) a second dispersion having a viscosity of about 45,000–65,000 cps. While it is convenient to provide polysiloxane oligomers for this purpose having methyl substituents, other substituents may also be included in the compositions in accordance with this invention. Thus, alkyl, aryl, halogen, and other substituents may be included in greater or lesser degree as part of the vinyl polysiloxanes which are useful. Those of ordinary skill in the art will be able to determine which polysiloxane materials are preferred for any particular utility from the foregoing considerations.

The quadri-functional polysiloxanes, designated and known in the art as QM resins, provide improved tear strength to the polymerized impression composition, by increasing its resulting polymerized crosslink density. As is known, the QM resin is made up of: Q units of quadri-functional $SiO_{4/2}$; and M units, such as $R^1R^2{}_2SiO_{1/2}$ wherein $R^1$ is unsaturated, preferably vinyl and $R^2$ is alkyl, aryl or the like, such as methyl, ethyl or phenyl. In a preferred composition $R^1$ is vinyl and both $R^2$ are methyl. A most preferred composition is represented by the formula:

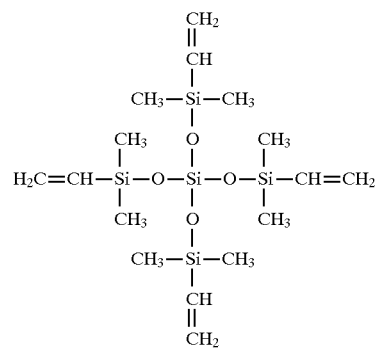

The QM resin provides a vinyl concentration in the dispersions with the vinyl-terminated polydivinylsiloxanes of at least about 0.16 m-mole/g. Preferably the vinyl concentration is 0.16–0.24 m-mole/g. The amount of QM resin is preferably about 20–25% by weight of the dispersion. Such dispersions are sold by Miles, Inc. of Pittsburg, Pennsylvania. Other QM resin formulations may be used, including those that are "neat" or dispersed in carriers other than the preferred fluid polydivinylsiloxane.

A key element of the invention is a retarder component that delays onset of polymerization of the QM resin/dispersion such that sufficient working times to employ the composition are provided. It functions, as it is consumed, to offset what would otherwise be a too rapid polymerization. The preferred retarder fluid in the preferred impression material of interest is 1,3 divinyltetramethyldisiloxane at a sufficient concentration level to perform its retarding functions, which is in at least about 0.03 weight percent of the composition, preferably within a range of about 0.03 to 0.12 weight percent. This preferred amount is in contrast with the lower amounts of 0.0015–0.020 weight percent typically employed in PVS systems to stabilize compositions. Other suitable retarders are any low molecular weight, vinyl functional material that would be initially consumed in the polymerization, to delay hardening suitably and as desired, including linear and cyclic polysiloxanes.

The organohydrogen-polysiloxanes useful in the practice of the present inventions are well-known to those of ordinary skill in the art. It is required only that polysiloxanes having hydrogen atoms directly bonded to silicone atoms be employed, and that they have suitable viscosities and other physical properties. Substituents in the molecules such as alkyl (especially methyl), aryl, halogen, and others may be employed as well. It is necessary only that such substituents not interfere with the platinum-catalyzed addition reaction. It is preferred that molecules be employed having at least two silicone-bonded hydrogen atoms per molecule. Polymethylhydrogensiloxane is preferred, having a viscosity range of about 35–45 cps.

The catalysts which are useful for catalyzing the reaction of the silicone atoms (bonded to hydrogen atoms) to the vinyl groups of the vinyl polysiloxane molecules are preferably based upon platinum. In this regard, it is preferred to employ a platinum compound such as chloroplatinic acid, preferably in admixture or complex with one or more vinyl materials, especially vinyl polysiloxanes. While such materials have been found to be preferred, other catalysts are also useful. Thus, platinum metal together with other noble metals including palladium, rhodium, and the like and their respective complexes and salts are also useful. In view of the toxicological acceptability of platinum, however, it is greatly to be preferred for dental use.

The compositions of the present invention also include a filler, preferably a mixture of hydrophobic fillers. A wide variety of inorganic, hydrophobic fillers may be employed such as silicas, aluminas, magnesias, titanias, inorganic salts, metallic oxides and glasses. It is preferred, however, that forms of silicone dioxides be employed. In accordance with the present invention, it has been found to be preferable to employ mixtures of silicone dioxides, including those derived form: crystalline silicone dioxide, such as pulverized quartz (4–6$\mu$); amorphous silicone dioxides, such as a diatomaceous earth (4–7$\mu$); and silanated fumed silica, such as Cab-o-Sil TS-530 (160–240 m$^2$/g), manufactured by Cabot Corporation. The sizes and surface areas of the foregoing materials are controlled to control the viscosity and thixotropicity of the resulting compositions. Some or all of the foregoing hydrophobic fillers may be superficially treated with one or more silanating or "keying" agents, as known to those of ordinary skill in the art. Such silanating may be accomplished through use of known halogenated silanes or silazides. The fillers are present, preferably, in amounts of from about 15 to about 45 weight percent of the composition, forming an impression composition that is polymer rich and, thus, having improved flow properties. The fillers, more preferably, are about 35–40 weight percent of the composition. A preferred filler mixture for a higher viscosity formulation includes 14–24 weight percent crystalline silicone dioxide, 3–6 weight percent amorphous silicone dioxide and 4–8 weight percent silanated fumed silicone dioxide. A most preferred filler is about 19% cristobalite at about 4–6$\mu$particle diameter, about 4% diatomaceous earth at about 4–7$\mu$particle diameter and about 6% silanated fumed silica at about 160–240 m$^2$/g.

A chemical system may be employed to diminish the presence or degree of hydrogen outgassing which may be typically generated as a result of the vinyl polymerization. The composition thus may comprise a finely divided platinum metal that scavenges for and takes up such hydrogen. The Pt metal may be deposited upon a substantially insoluble salt having a surface area of between about 0.1 and 40m$^2$/g. Suitable salts are barium sulphate, barium carbonate and calcium carbonate of suitable particle sizes. Other substrates include diatomaceous earth, activated alumina, activated carbon and others. The inorganic salts are especially preferred to lend improved stability to the resulting materials incorporating them. Dispersed upon the salts is about 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones.

An important improvement of the invention is inclusion in the composition of a surfactant that imparts wettability to said composition, as indicated by a surface contact angle with water at three minutes of less than 50°. An unexpected result of the selection of surfactant provides a major clinical advantage in that the wetting contact angle of less than 50° is achieved in less than about two minutes, decreasing and remaining below 50° throughout the working time of the composition, in contrast with prior art polyvinylsiloxanes and surfactant formulations that require more time to wet out. This higher wetting rate of the composition of the invention is particularly advantageous during the impression taking process and is shown in the Drawings.

Figure 2:
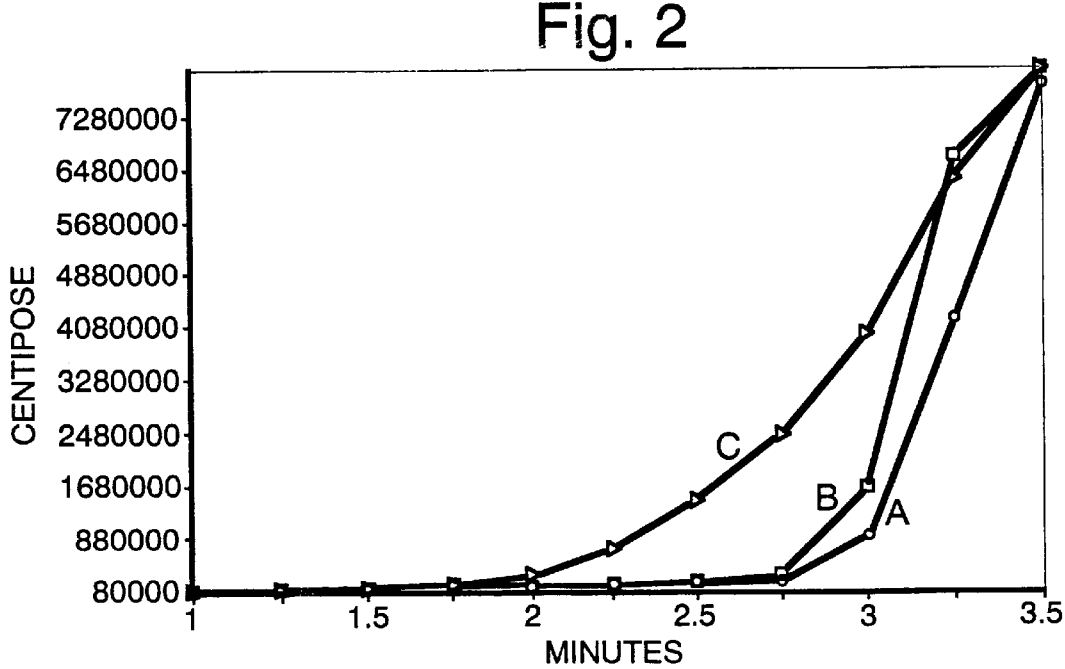
FIG. 2 is a graph showing Impression Material Viscosity as a function of Time, in minutes.

Referring to FIG. 1, the Wetting Contact Angle, in degrees, as a function of Time, in minutes, is shown for the polyvinyl siloxane composition of the invention, in comparison with prior art compositions. Curve A is the composition of the invention showing a wetting contact angle of about 50° at two minutes after mixing of the base and catalyst components. FIG. 1 demonstrates that good wettability is achieved early and improves at a fast rate over the about 3.5 minutes of useful working life of the impression taking material. Curves B and C are, respectively, polyether and conventional polyvinyl siloxane impression materials of the prior art. FIG. 2 shows Impression Material Viscosity as a function of Time for composition of the invention, Curve A, and the two prior art compositions B and C noted above. It shows the progression of the polymerization process from mixing and, in combination with FIG. 1, demonstrates that the improved wettability of the composition of the invention occurs during the critical working time for the impression material, an important advantages over other known systems.

The surfactant of the invention may be of cationic, anionic, amphoteric or nonionic type. A key criteria for selection is that the Hydrophobic Liphophilic Balance (HLB) value (described by Gower, "Handbook of Industrial Surfactants", 1993) must be in the range of 8–11. As is well-known, the higher the HLB the more hydrophobic is the substance. In addition, the pH of the surfactant must be in the 6–8 range to prevent side reactions that may be detrimental the polymerization of the impression. A preferred surfactant is nonionic, having an HLB value of 10.8 comprising nonylphenoxypoly(ethyleneoxy) ethanol, sold by Rhone-Poulenc of Cranbury, NJ as Igepal CO-530. In comparison it is noted above with respect to Bryan et al, in U.S. '959 that Igepal CO-630, having an HLB of 13.0, differing in structure from CO-530 wherein the number of repeating units in CO-630 is 9 and those of CO-530 is 6, is not effective, demonstrating the criticality of the HLB limitation. The amount of surfactant used to render the composition hydrophilic is based on the rate of wetting. The desired contact angle at three (3) minutes is less than about 50°.

The composition of the invention may include plasticizers for the higher viscosity material that beneficially alter the handling and flow properties of the impression material, particularly the catalyst component. A preferred emulsifying plasticizer is octyl benzyl phthalate. Other phthalates are useful. The plasticizer composite is not necessary for lower viscosity wash type impression materials.

The selection of QM resin dispersion viscosity depends upon the overall impression material characteristics desired. To give higher viscosity handling characteristics more of the 60,000 cps component is employed. For a low viscosity type, more of the 6,000 cps component is employed to increase flow. In addition to the QM resin dispersion characteristics filler selection affects overall viscosity characteristics. Using a higher loading of low surface area fillers, such as cristobalite, gives more flow to a low viscosity type impression material. Using a higher loading of high surface area fillers, such as diatomaceous earth, reduces flow and gives more body to a high viscosity type impression material. The use of an emulsifying plasticizer makes the composition more thixotropic, which is useful for a high viscosity material. However, a plasticizer is generally not used in the low viscosity material since high flow is desired.

The composition of the invention may include various pigments to achieve a preferred color. Such pigments are well known and include titanium dioxide as well as many others.

The two component compositions prepared in accordance with the instant invention are employed in the same way that conventional impression materials have been employed. Thus, appropriately equal portions of base paste and catalyst paste are mixed together thoroughly and applied to the oral dentition or other region for a period of time sufficient for the polymerizations or hardening of the composition. Once the composition has been substantially hardened, it is removed from the mouth or other surface and used for the elaboration of casts and the like from which representations of the casting surface are subsequently prepared.

As will be appreciated by those of ordinary skill in the art, it is important that dental silicone materials be capable of being stored for reasonably long periods of time and at reasonable storage temperature in order to maximize their commercial utility. Accordingly, it is necessary that such materials not suffer from decreased physical properties or substantial changes in working time or hardening time upon such storage. In this regard, accelerated storage tests employing high ambient temperatures are now capable of determining the shelf stability of such materials.

Certain embodiments of the present invention are described below. Numerous other compositions and formulations may be prepared within the spirit of the invention. The following examples are not to be construed as limiting and are offered by way of illustration.

EXAMPLE 1

A two component composition of the invention is formulated in a Base Paste and Catalyst Paste components. Mixing of each component's ingredients is done in a double planetary mixer having a mixing pot heated with circulating water at 45° C.-50° C. and under 65 mm mercury vacuum.

BASE PASTE COMPONENT

In making the Base Paste, the mixing pot is first charged with all organohydrogen polysiloxane and incrementally thereafter, with QM dispersion and filler component, with mixing continuing until a uniform mixture is achieved. The finished Base Paste is discharged into a storage container.

CATALYST PASTE COMPONENT

The Catalyst Paste component is formulated and mixed under conditions and in equipment as described above. The platinum catalyst, 1,3 divinyldimethyldisiloxane, QM resin dispersions, fillers and pigments are added incrementally to the mixing pot and mixing carried out until a uniformly mixed mass is achieved. The compounded Catalyst Paste is then discharged into a storage container.

The composition of each component is indicated in the table below, wherein amounts are in weight percent of the component.

|  | BASE | CATALYST |
|---|---|---|
| Organohydrogen Polysiloxane | 9.00 | 0.00 |
| (5000–7000 cps) QM resin dispersion | 19.62 | 23.95 |
| (45000–60000 cps) QM resin dispersion | 34.59 | 42.89 |
| Cristobalite | 19.01 | 19.06 |
| Diatomaceious earth | 6.53 | 6.41 |
| Cab-O-Sil TS-530 | 6.53 | 6.00 |
| Pigments Predispersed in Divinyl Polysiloxane | 0.65 | 0.25 |
| Titanium Oxide Pigment | 0.07 | 0.07 |
| Surfactant (Igepal CO-530) | 4.00 | 0.00 |
| Plasticizer | 0.00 | 0.50 |
| Platinum Catalyst | 0.00 | 0.64 |
| 1,3-Divinyldimethyidisiloxane | 0.00 | 0.07 |
| Finely divided Platinum metal on Calcium Carbonate | 0.00 | 0.16 |
|  | 100.00 | 100.00 |

EXAMPLE 2

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.00 | 0.00 |
| (5000–7000 cps) QM resin dispersion | 20.18 | 31.71 |
| (45000–60000 cps) QM resin dispersion | 35.61 | 35.23 |
| Cristobalite | 19.74 | 20.67 |
| Diatomaceious earth | 4.30 | 4.28 |
| Cab-O-Sil TS-530 | 6.45 | 6.42 |
| Pigments Predispersed in Divinyl Polysiloxane | 0.65 | 0.25 |
| Titanium Oxide Pigment | 0.07 | 0.07 |
| Surfactant (Igepal CO-530) | 4.00 | 0.00 |
| Plasticizer | 0.00 | 0.50 |
| Platinum Catalyst | 0.00 | 0.64 |
| 1,3-Divinyldimethyidisiloxane | 0.00 | 0.07 |
| Finely divided Platinum metal on Calcium Carbonate | 0.00 | 0.16 |
|  | 100.00 | 100.00 |

EXAMPLE 3

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 10.00 | 0.00 |
| (5000–7000 cps) QM resin dispersion | 14.73 | 26.91 |
| (45000–60000 cps) QM resin dispersion | 43.80 | 43.80 |
| Cristobalite | 17.00 | 17.40 |
| Diatomaceious earth | 5.00 | 5.00 |
| Cab-O-Sil TS-530 | 5.00 | 5.00 |
| Pigments Predispersed in Divinyl Polysiloxane | 0.40 | 0.50 |
| Titanium Oxide Pigment | 0.07 | 0.07 |
| Surfactant (Igepal CO-530) | 4.00 | 0.00 |
| Plasticizer | 0.00 | 0.50 |
| Platinum Catalyst | 0.00 | 0.65 |
| 1,3-Divinyldimethyidisiloxane | 0.00 | 0.07 |

-continued

|  | BASE | CATALYST |
|---|---|---|
| Finely divided Platinum metal on Calcium Carbonate | 0.00 | 0.10 |
|  | 100.00 | 100.00 |

EXAMPLE 4

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 10.00 | 0.00 |
| (5000–7000 cps) QM resin dispersion | 19.40 | 32.37 |
| (45000–60000 cps) QM resin dispersion | 36.03 | 36.03 |
| Cristobalite | 20.00 | 20.00 |
| Diatomaceious earth | 5.00 | 5.00 |
| Cab-O-Sil TS-530 | 5.00 | 5.00 |
| Pigments Predispersed in Divinyl Polysiloxane | 1.50 | 0.00 |
| Titanium Oxide Pigment | 0.07 | 0.07 |
| Surfactant (Igepal CO-530) | 3.00 | 0.00 |
| Plasticizer | 0.00 | 0.50 |
| Platinum Catalyst | 0.00 | 1.00 |
| 1,3-Divinyldimethyidisiloxane | 0.00 | 0.03 |
| Finely divided Platinum metal on Calcium Carbonate | 0.00 | 0.00 |
|  | 100.00 | 100.00 |

EXAMPLE 5

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 11.00 | 0.00 |
| (5000–7000 cps) QM resin dispersion | 14.36 | 28.44 |
| (45000–60000 cps) QM resin dispersion | 43.07 | 42.64 |
| Cristobalite | 17.00 | 17.19 |
| Diatomaceious earth | 5.00 | 4.95 |
| Cab-O-Sil TS-530 | 5.00 | 4.95 |
| Pigments Predispersed in Divinyl Polysiloxane | 1.50 | 0.00 |
| Titanium Oxide Pigment | 0.07 | 0.07 |
| Surfactant (Igepal CO-530) | 3.00 | 0.00 |
| Plasticizer | 0.00 | 0.49 |
| Platinum Catalyst | 0.00 | 1.13 |
| 1,3-Divinyldimethyidisiloxane | 0.00 | 0.06 |
| Finely divided Platinum metal on Calcium Carbonate | 0.00 | 0.09 |
|  | 100.00 | 100.00 |

EXAMPLE 6

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Tergitol 15-S-3) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal on Calcium Carbonate | 0.00 | 0.08 |
|  | 100.00 | 100.00 |

EXAMPLE 7

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-630) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal on Calcium Carbonate | 0.00 | 0.08 |
|  | 100.00 | 100.00 |

EXAMPLE 8

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-210) | 4.76 | 0.00 |
| Plasticizer | 0.48 | 0.48 |
| Platinum Catalyst | 0.00 | 0.48 |

-continued

| | BASE | CATALYST |
|---|---|---|
| 1,3-Divinyldimethyidisiloxane | 0.00 | 0.05 |
| Finely divided Platinum metal on Calcium Carbonate | 0.00 | 0.08 |
| | 100.00 | 100.00 |

EXAMPLE 9

A two component composition of the invention is made by first making a Base Paste and then a Catalyst Paste as described in Example 1, having the composition indicated in the table below.

| | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-430) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal on Calcium Carbonate | 0.00 | 0.08 |
| | 100.00 | 100.00 |

EXAMPLE 10

A two component composition of the invention is made by first making a Base Paste and then a Catalyst Paste as described in Example 1, having the composition indicated in the table below.

| | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-530) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal on Calcium Carbonate | 0.00 | 0.08 |
| | 100.00 | 100.00 |

EXAMPLE 11

A representative sample of each of the above described Examples, of 10 grams, is mixed in equal parts and the properties of the mixture and resulting polymerized composition tested. The table below reports the results said measurements. The first five properties reported are tested in accord with ADA Specification 19: Non-Aqueous Elastomer Impression materials (1976, as amended in 19a of 1982).

The following procedure was used to provide tensile tear strength, percent elongation, and modulus of elasticity of the Examples.

Equal parts of the base and catalyst components are mixed and the samples or specimen is placed in a specimen mold having an I-shaped cavity that is 1.5 mm thick, 20 mm×11 mm, with top arms of 8 mm depth and center I portion 5 mm wide. The filled mold is clamped between two stainless steel plates and the assembly is placed in a 32° C. water bath. At six minutes from start of mix, the assembly is removed from the bath. The mold is unclamped, the specimen is removed from the mold and any flash is removed from the specimen. At 10 minutes from start of mix the specimen is clamped into the specimen test grips of an Instron Model 1123 in the extension mode. The Instron is attached to a Microcon II micropressor that has been programmed to calculate the tear strength [psi],% elongation, and modulus of elasticity. At 11 minutes, the specimen is stressed by the Instron at a rate of 10 mm/min. until the specimen reaches peak failure. (The maximum load is set to 5 kg.) This is repeated for five specimens and then statistically evaluated results are reported, as shown in Table I.

Wetting contact angles are measured for each Example as follows. One gram (1g) of base and one gram (1g) of catalyst paste are mixed together until uniform (~30 seconds). A one-half gram (0.5g) of mixed paste is placed between two sheets of polyethylene (Dentsilk) and pressed flat using a glass plate, about 2–3 mm thick. The specimen is allowed to stand undisturbed until set (~15 minutes). The polyethylene sheets are removed, being careful not to touch the surface of the specimen, and the specimen placed on the table of a gynometer, a well known device for measuring contact angles. The eyepiece recticle is adjusted to the horizontal and vertical planes of the specimen surface and stop watch is started as a drop of water is dropped onto the specimen surface. At 1.5 minutes to 3.5 minutes, the inside contact angle, in degrees, of the water/specimen interface is measured using the gynometer scale, recorded for the specimen and reported in Table I hereinbelow.

TABLE I

PROPERTIES OF EXAMPLES

| Property | \multicolumn{10}{c}{Examples} | | | | | | | | | |
|---|---|---|---|---|---|---|---|---|---|---|
| | 1 | 2 | 3 | 4 | 5 | 6 | 7 | 8 | 9 | 10 |
| Work Time (min) | 3 | 3 | 3 | 2 | 3 | 4.25 | 2.50 | 3.33 | 3.18 | 2.50 |
| Set | 6 | 6 | 6 | 4 | 6 | 9 | 5 | 7 | 7 | 5.75 |
| % Deformation | 0.5 | 0.25 | 0.45 | 0.3 | 1.9 | 4.25 | 1.7S | 2.25 | 23 | 1.65 |
| % Strain | 2.75 | 3.15 | 3.25 | 2.75 | 3.5 | NA | NA | NA | NA | NA |
| Consistency (mm) | 33 | 34 | 36 | 32 | 38 | 33 | 29 | 32 | 31 | 30 |
| Contact Angle with water at 3 min. (°) | 30 | 35 | 38 | 37 | 42 | 28 | 52 | 56 | 42 | 31 |
| Tear Strength PSI | 277 | 277 | 295 | 289 | 216 | NA | NA | NA | NA | NA |

Examples 1–3 are preferred compositions. Example 1 is suitable for dispensing from a tube and hand mixing. Example 2 is most preferred for cartridge dispensing and static-mixing. Example 3 describes a composition of the invention that is suitable for forming a lower viscosity composition suitable for either tube or cartridge dispensing.

The composition of Example 4, having a high viscosity, exhibited severe gassing, having a higher hydride concentration and no degassing component. Example 5, having a low viscosity, demonstrated good syringe consistency but had a high percent deformation and percent strain while tear strength was lower. This composition had a high hydride, low surfactant, low retarder and low catalyst concentration. Compositions of Examples 6, 8 and 9 did not polymerize properly. The composition of Example 6 had too low retarder and catalyst contents. The surfactant was also too high an HLB and too acid. The composition of Example 7 lacked wetting capability having a surface contact angle exceeding desirable limits. Examples 8 and 9 both were too low in retarder and catalyst concentrations The composition of Example 10 exceeded desired percent deformation.

EXAMPLE 12

A two component composition of the invention, having the composition indicated below, is made as described in Example 1. A higher content of lower viscosity QM resin dispersion is utilized to form a low viscosity-wash formulation. Also additional surfactant is employed while no plasticizer is necessary.

| | BASE | CATALYST |
|---|---|---|
| Organohydrogen Polysiloxane | 8.0 | — |
| (5000–7000 cps) QM resin dispersion | 28.7 | 39.6 |
| (45000–60000 cps) QM resin dispersion | 12.3 | 16.7 |
| Cristobalite | 32.0 | 39.6 |
| Diatomaceious earth | — | — |
| Cab-O-Sil TS-530 | 3 | 3 |
| Pigments Predispersed in Divinyl Polysiloxane | 1 | — |
| Titanium Oxide Pigment | — | — |
| Surfactant (Igepal CO-530) | 7.5 | — |
| Plasticizer | — | — |
| Platinum Catalyst | — | 0.36 |
| 1,3-Divinyldimethyidisiloxane | — | 0.11 |
| Finely divided Platinum metal on Calcium Carbonate | — | 0.60 |
| Dried Calcium Sulfate | 5.0 | — |
| Organic Pigments | 2.5 | — |
| Total | 100.00 | 100.00 |

EXAMPLE 13

A two component composition, having the composition indicated below, is made as described in Example 1. The resulting formulation is a low viscosity wash impression material.

| | BASE | CATALYST |
|---|---|---|
| Organohydrogen Polysiloxane | 9.0 | 0 |
| (5000–7000 cps) QM resin dispersion | 13.2 | 29.6 |
| (45000–60000 cps) QM resin dispersion | 47.27 | 47.27 |
| Cristobalite | 14.0 | 14.0 |
| Diatomaceious earth | 4 | 4 |
| Cab-O-Sil TS-530 | 4 | 4 |
| Pigments Predispersed in Divinyl Polysiloxane | 1 | — |
| Titanium Oxide Pigment | 0.035 | 0.035 |
| Surfactant (Igepal CO-530) | 5 | — |
| Plasticizer | — | — |
| Platinum Catalyst | — | 0.28 |
| 1,3-Divinyldimethyidisiloxane | — | 0.014 |
| Finely divided Platinum metal on Calcium Carbonate | — | 0.8 |
| Dried Calcium Sulfate | — | — |
| Organic Pigments | 2.5 | — |
| Total | 100.00 | 100.00 |

EXAMPLE 14

A two component composition, having the composition indicated below, is made as described in Example 1. The resulting formulation is a low viscosity wash impression material.

| | BASE | CATALYST |
|---|---|---|
| Organohydrogen Polysiloxane | 7.5 | 0 |
| (5000–7000 cps) QM resin dispersion | 35.56 | 44.89 |
| (45000–60000 cps) QM resin dispersion | 11.84 | 14.97 |
| Cristobalite | 29 | 31.63 |
| Diatomaceious earth | 0 | — |
| Cab-O-Sil TS-530 | 3 | 3 |
| Pigments Predispersed in Divinyl Polysiloxane | 0.9 | — |
| Titanium Oxide Pigment | — | — |
| Surfactant (Igepal CO-530) | 5 | — |
| Plasticizer | — | — |
| Platinum Catalyst | — | 0.55 |
| 1,3-Divinyldimethyidisiloxane | — | 0.056 |
| Finely divided Platinum metal on Calcium Carbonate | — | 0.5 |
| Dried Calcium Sulfate | 5 | 5 |
| Organic Pigments | 2.2 | 0 |
| Total | 100.00 | 100.00 |

EXAMPLE 15

The testing procedures of in Example 11 were applied to representative samples of the formulations of Examples 12–14. Table II below reports the results of the measurements.

TABLE II

| Property | Examples | | |
|---|---|---|---|
| | 12 | 13 | 14 |
| Work Time (min) | 2.92 | 3.33 | 3.50 |
| Set Time (min) | 5.67 | 7.25 | 7.00 |
| % Deformation | 0.45 | 1.85 | 1.20 |
| % Strain | 3.9 | 6.0 | 4.2 |
| Consistency (mm) | 40 | 41 | 40 |
| Contact Angle with water at 3 min. (°) | 33 | 50 | 40 |
| Tear Strength (PSI) | 200 | 166 | 220 |

The dental impression material according another embodiment of the invention is a two component system on the basis of addition curing silicones as follows:
from about 45 to 55 percent by weight based upon 100 percent by weight of the impression material of a base paste. The base paste includes:
a1. from about 1 to about 10 percent by weight based upon 100 percent by weight of the base paste of a linear dimethylvinyl terminated polydimethylsiloxane,
a2. from about 8 to about 20 percent by weight based upon 100 percent by weight of the base paste of linear dimethyl-(H-methyl)-siloxane copolymers with trimethylsilyl or dimethylhydrosilyl termination,
a3. from about 15 to about 25 percent by weight based upon 100 percent by weight of the base paste of dimethylvinylsilyl terminated polydimethylsiloxane containing 15–25% by weight highly dispersed $SiO_2$,
a4. from about 50 to about 60 percent by weight based upon 100 percent by weight of the base paste of low molecular weight QM-resins optionally containing functional groups reactive in the hydrosilylation reaction and ethoxy groups and being homogeneously soluble in al and including $SiO_{4/2}$, $RO_{1/2}$ and $R_3SiO_{1/2}$ in which R represents n-alkyl, phenyl or vinyl and has an alkoxy group content from less than 4 mmol/g,
a5. a scavenger for adsorption of water from both the ingredients and the environment,
a6. from about 0 to about 10 percent by weight based upon 100 percent by weight of the base paste of linear dimethyl-(vinylmethyl)-siloxane copolymers with dimethylvinylsilyl terminations,
a7. dipolar surfactant to improve wetting properties,
a8. and optionally, pigments.
The impression material also includes from about 45 to about 55 percent by weight of a catalyst paste which includes:
b1. from about 1 to about 5 percent by weight based upon 100 percent by weight of the catalyst paste of linear dimethylvinyl terminated polydimethylsiloxanes,
b2. from about 30 to about 35 percent by weight based upon 100 percent by weight of the catalyst paste of dimethylvinylsilyl terminated polydimethylsiloxanes containing 20–35% highly disperse $SiO_2$
b3. from about 55 to about 70 percent by weight based upon 100 percent by weight of the catalyst paste of low molecular weight QM-resins optionally containing functional groups reactive in the hydrosilylation reaction and ethoxy groups and being homogeneously soluble in al and comprises $SiO_{4/2}$, $RO_{1/2}$, and $R_3SiO_{1/2}$ in which R represents n-alkyl, phenyl or vinyl and has an alkoxy group content from less than 4 mmol/g b4. from about 0 to about 10 percent by weight based upon 100 percent by weight of the catalyst paste of linear dimethyl-(vinylmethyl)-siloxane copolymers with dimethylvinylsilyl termination's,
b5. from about 0.5 to about 1.5 percent by weight based upon 100 percent by weight of the catalyst paste of Pt-catalyst prepared from $H_2PtCl_6$ and tetramethyldivinyldisiloxane
b6. short chained dimethylvinylsilyl terminated polydimethylsiloxanes (n=0–5).
b7. $H_2$-adsorbent; and optionally
b8. pigments.
All "%" and "percent" are by weight. A low viscosity type dental impression material is provided having the flow characteristics under clinical conditions combined with a high tear strength to maintain the subgingival undercuts. "Low" viscosity as used herein means that of type 3 accordingly to ISO 4823. These characteristics are demonstrated by the following physical parameter:
Viscosity:
$h_{[200\ Pa]}$=5.0–15.0 Pas for single pastes
$h_{[200\ Pa]}$=15.0–25.0 Pas for the mix
and a yield stress of: $\theta_{[0-10\ Pa]}$ less than about 5.0 Pa contact angle: less than about 45° tear strength: greater than about 1.5 MPa Wherein al and bi are characterised as vinyl terminated dimethyl polysiloxanes according to the formula

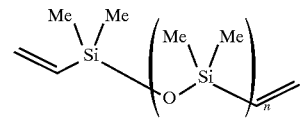

specified with a viscosity in the range of 0.2–200 Pas at 20° C. and vinyl content of 0.01–0.5 mval/g. The letter "n" represents an integer of from 50 to about 1300, although this is not an absolute limitation of the invention. The component a2 is characterised as an organpolysiloxane according to the formula

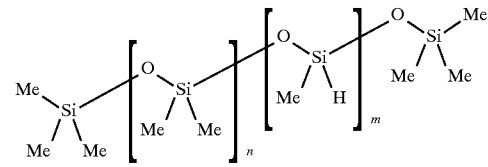

having at least three Si-bonded hydrogen atoms per molecule. Suitably, this organopolysiloxanes contain 2.0–8.5 mval/g of active SiH-units.

The components a3 and b2 are characterised as an aerosil containing organopolysiloxane terminated with dimethylvinylsilyl endgroups. Examples are those prepared according to DE-A 2,535,334, which is hereby incorporated by reference.

The components a4 and b3 are characterised in that they contain tetrafunctional $SiO_{4/2}$ as Q-moieties and monofnctional $R_3SiO_{1/2}$ as M-units, in which R can be alkyl aryl or alkenyl most preferably methyl or vinyl. Moreover, trifunctional $RSiO_{3/2}$ (silsesquioxane-units or T-units) and $R_2SiO_{2/2}$ as D-units can be present wherein the content of these QM-units has to be higher than about 10%.

Component a5 is selected from water absorbing inorganic fillers such as calcium sulphate hemihydrate, anhydrous calcium sulphate calcium chloride and the like, and absorbing compounds as zeoliths type a molecular sieves and other similar absorbing and adsorbing compounds. A zeolith type A in a content of from about 0.5 to about 10% by weight of the base paste is one preferred scavenger.

The components a6 and b6 are characterised as the product of a copolymerization reaction of dimethyl-dihalogenosilanes or dimethyldialkoxysilanes with methylvinyl dihalogenosilanes or methylvinyl dialkoxysilanes leading to a copolymer according to the formula

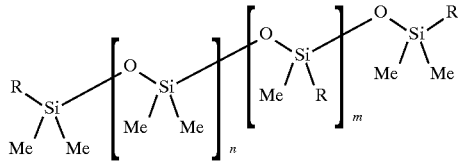

with wherein R is as above preferably a vinyl giving a vinyl content of 0.5–3.0 mval/g, and a viscosity of $\eta(20° C.)=200$ mPas–10,000 mPas. One preferred R group is $(CH_2)_3$—O—$[CH_2CH_2$—$O]_x$—$CH_3$ where x is an integer of from about 2 to about 10.

Component a7 is characterised as nonylphenoxy poly (ethyleneoxy)-ethanol, and b5 is characterised as the product of the reaction of hydrous chloroplatinic acid with tetramethyldivinyldisiloxane.

Component b7 is characterised as highly disperse platinum or palladium on charcoal, calciumsulfate, alumina or zeoliths.

A combination of ingredients according to the invention combines a very high tear strength together with highly hydrophilic properties and good flow and wetting characteristics.

The combination of ingredients according to the invention promotes low consistency of both the single paste and the mix. The base pastes according to the invention show a non Newtonian flow behaviour with a stress dependent viscosity and a thixotropic effect. Even with a high content of surfactant (Examples A, B and D below) the yield stress of the base paste, resulting by rheological substructures, is much lower as in the case of usual light body formulations (Example F).

Figure 3:
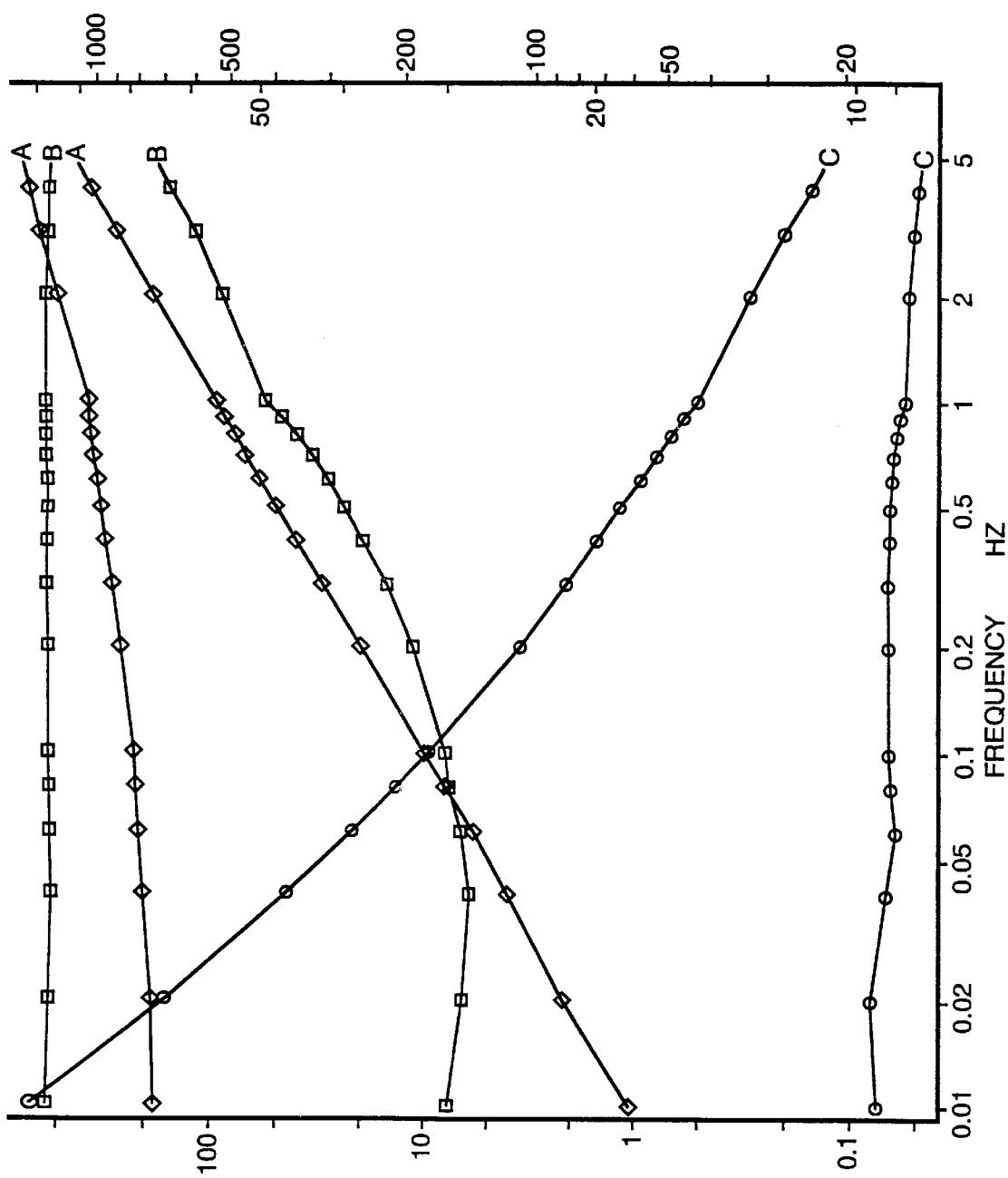
FIG. 3 is a graph showing the difference in the charcteristics of the base and catalyst components of the present invention.
Figure 4:
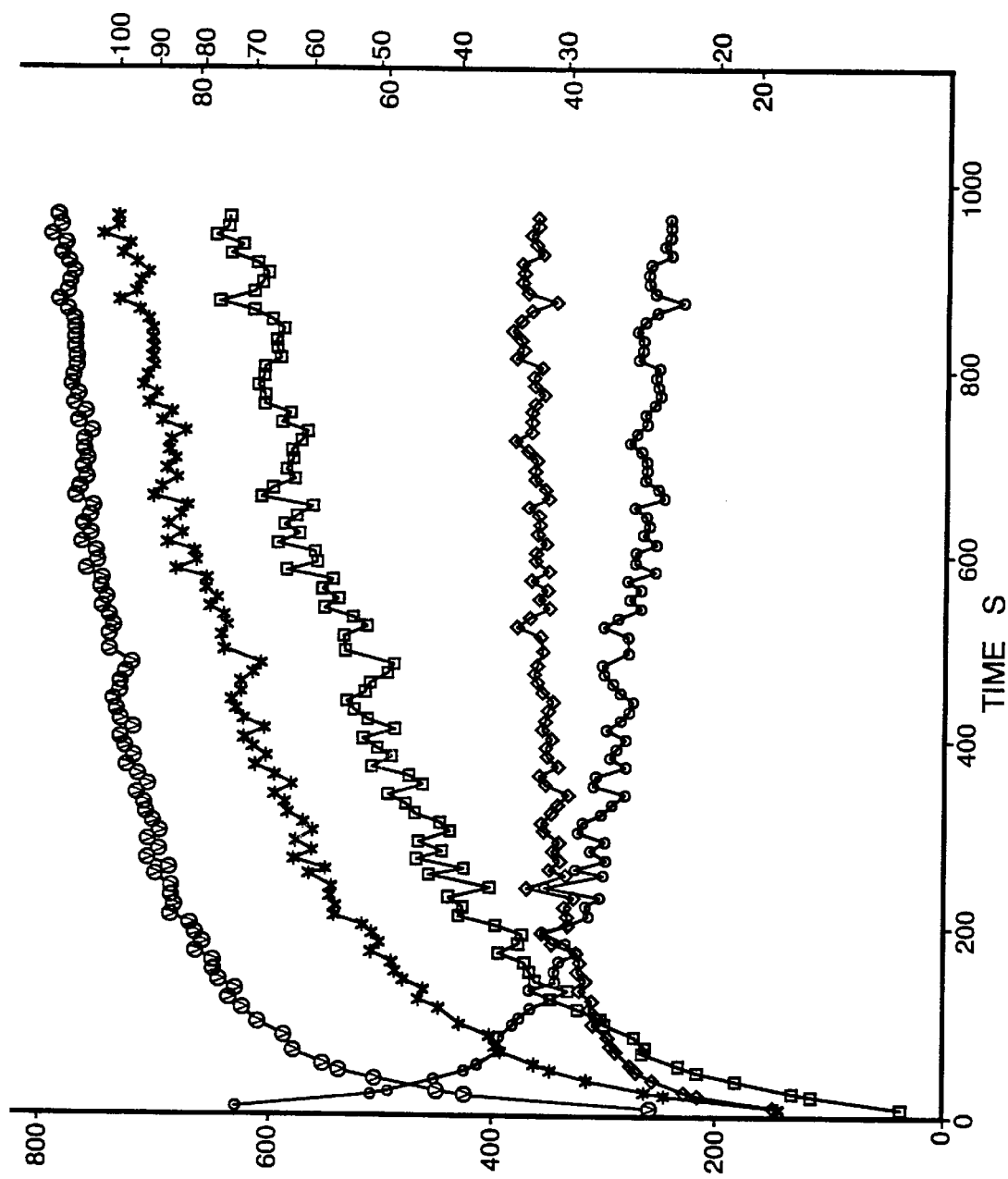
FIG. 4 is a graph showing the thixotropy of a base paste according to the invention by a time sweep measured with an oscillation rheometer.
Figure 5:
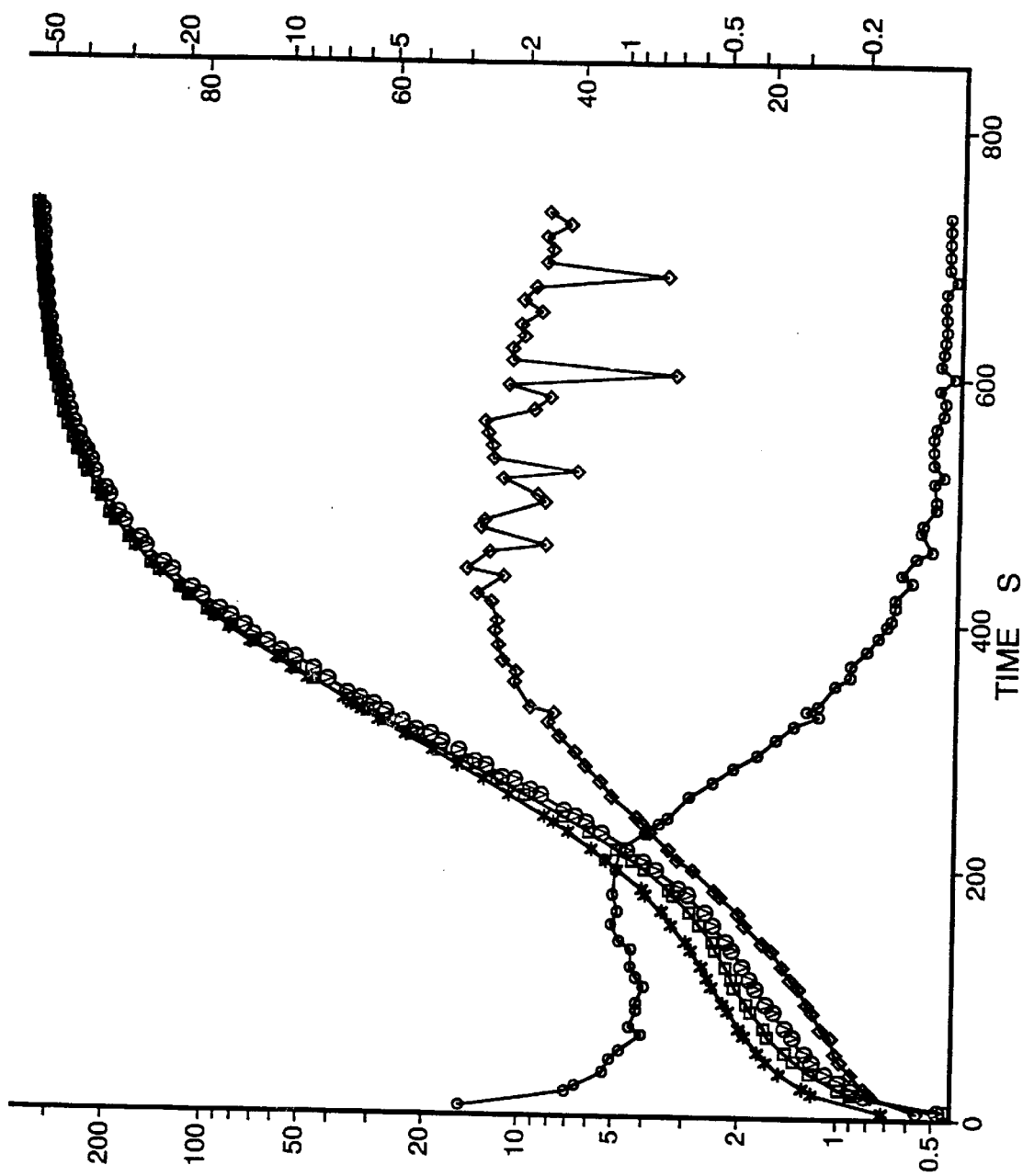
FIG. 5 is a graph representing the development of viscosity during the setting reaction of the material accorindg to the invention by a time sweep with an oscillation rheometer.

In the disucssion to follow reference will be made to FIGS. 3–4 as were briefly discussed hereinabove. In FIG. 3, the x-axis shows the frequency omega in 1/s, and the two y-axis show the shear stress G'(left y-axis) in Pascal (Pa) and the viscosity n' in Pascal seconds (Pas) (left y-axis). In FIG. 4, the x-axis is time in seconds (s). The y-axis is again the shear strees G in Pa on the left y-axis. On the right y-axis, there are two parameters, the viscosity n' in kPas and the loss angle. The shear modulus G' of a fluid system is split into two parts. The storage modulus G' represents the elastic properties of the system, whereas the loss modulus G" represents the viscous properties. The loss angle, delta, represents the angle between G' and G" in the triangle developed by the axis, G' and G". FIG. 5 has the same x and y axis as FIG. 4.

Furthermore, in FIG. 3, the letter "A" represents the shear modulus G'; the letter "B" represents delta or the loss angle between G' and G"; and "C" represents n', the viscosity in Pas. In FIG. 4, the small circle graphical information represents delta; the letter "V" in a circle represents the viscosity; the astrics represent the shear stress G; the small squares represent the storage modulous G'; and the diamond shape represents information for the loss modulous G".

In FIG. 5, the graphical representations are the same as those in FIG. 4.

The catalyst paste according to the invention even with an aerosil content of 10% shows nearly Newtonian flow characteristics with constant viscosity of 10.0 Pas and no yield stress or thixotropic effect. The rheological properties of the single pastes according to the invention have been measured by a frequency sweep with an oscillation rheometer (CS-50 Fa. Bohlin) . FIG. 3 shows the difference between the non Newtonian flow characteristics of the Base and the quasi-Newtonian behaviour of the Catalyst.

The thixotropy of a base paste according to the invention can be shown by a time sweep measured with oscillation rheometer under non-disordering conditions. The sample was placed on the plate of a cone/plate measuring system. After lowering the upper plate a boost stress of 200 Pa was applied on the material for a period of 5 sec. to disturb the Theological substructure responsible for the yield stress. The relaxation of the elastic properties was measured by oscillation with a frequency of 1 Hz and a deformation of 0.0005 radian in periods of 10 sec. As can be seen in the graph of FIG. 4 at the beginning of the measurement the loss modulus (G") is higher than the storage modulus (G') and the paste behaves as a liquid. After the relaxation time of ca. 600 seconds (sec.) the substructure is rebuilt and the material shows elastic behaviour. By side of the typical relaxation time the gel point, when G"=G' is characteristic for the thixotropic behaviour of non Newtonian fluids. The time $t_g$(usm) for reaching this gel point is at least 90 sec. for a base paste according to the invention.

Because of the thixotropy of the base paste even with a yield stress and a highly stress dependent viscosity the material according to invention behaves like liquid that flows on the surface immediately after mixing by releasing out of the cartridge. When the two components are mixed by release through a static mixer the flow behaviour is mainly characterised by the catalyst paste, because immediately after mixing the Theological substructures in the base paste, responsible for the yield stress and the stress dependent viscosity, are disturbed by the shear stress of mixing.

The material according to the invention has been developed preferably for the application as a dental cartridge material. Because of the Theological properties of the material according to the invention only very low forces are necessary to release the material out of the cartridge. Therefore very small static mixers can be used to release the material according to invention out of the cartridge, resulting in a minimal rate of waste and a large reduction of costs for the user. By "low viscosity" herein, it is meant that according to ISO 4823.

To investigate the development of viscosity during the setting reaction of the material according to the invention a sample (Example B) was measured in a time sweep with an oscillation-rheometer (Fig. 5) . The material was released out of a cartridge (as used in dental applications) immediately on the plate of a cone/plate measuring system and the measurement was started 10 sec. after release. The first value of viscosity was registrated 15 sec. after release. The measurement was carried out under non disordering conditions with a frequency of 1 Hz, a deformation of 0.001 radians and a measuring period of 10 sec. Under these conditions the rheological substructures are not disturbed by the torque of the oscillation (as it can be shown in a amplitude sweep of both single pastes). As shown in FIG. 5 the viscosity rises very fast in the first period of the reaction. This effect can by explained by relaxation of the shear stress caused by the release out of the cartridge (thixotropic effect). At the beginning of the setting reaction the loss angle δ is higher than about 45°. That means at this time the material has no yield stress. As a liquid the material is able to flow on the surface of the teeth at low shear stress even under the influence from gravity, when it is syringed out of the cartridge.

Important for the kinetics of the setting reaction is at first the gel time $t_g$ (set material) and second the setting time $t_c$. The gel time $t_g$ (set material) is reached when the loss angle $\delta=\arctan(G''/G')$ has the maximum value. In cases when there is no maximum for the loss angle (when $\delta>45°$) the gel time is reached when the loss angle passes $45°$ ($G'=G''$). The setting time is reached when the storage modulus $G'$ has reached its plateau.

In the examples A and B according to the invention the formed network is partly interpenetrated by the existing network of QM-resins. This allows additional network strength. These QM-resins are characterised in that they contain tetrafunctional $SiO_{4/2}$ as Q-moieties and monofunctional $R_3SiO_{1/2}$ as M-units, in which R can be alkyl, aryl or alkenyl most preferably methyl or vinyl. Moreover, trifunctional $RSiO_{3/2}$ (silsesquioxane-units or T-units) and $R_2SiO_{2/2}$ as D-units can be present. The content of these QM-resins is preferably higher than about 10%. A lower content as in the case of Example E is not sufficient to increase the tear strength.

Alternative to the use of a high QM-resin content as in Examples A and B, highly functional vinyl-silicones are used in Example D. In this material according to the invention the high tear strength is a result of a high content of reactive vinyl groups in both components. In usual addition curing silicones these reactive functionalities are only placed at the end of long chained polydimethyl siloxanes. In the material according to the invention additional vinyl groups are placed on the chain of these polymers. These additional functionalities lead to a higher network density combined with reinforced mechanical strength. In this case a high content of QM-resins is not necessary.

Adding a filler to reinforce the mechanical strength is not necessary in the case of a material according to the invention. The fillers used are only necessary to adjust the Theological properties and to adsorb moisture from the surfactant or environment. Even with a filler content of less than 15% by weight the material according to the invention (Examples A, B and D) has a higher tear strength than conventional highly filled light bodies (filler content greater than 40% by weight, Example F). In combination with a high strain in compression the improved mechanical strength is able to maintain the subgingival undercuts.

To improve the wetting properties a high amount of surfactant has been added to the material according to the invention in order to achieve a very low contact angle to water. The surfactants are the same as earlier described. Surprisingly these high amounts of surfactant lead to only a very low yield stress of less than 5 Pa in the case of the base paste (Examples A, B and D). Conventional light bodies (Example F) have higher yield stresses with even lower content of surfactant. As it is seen in FIG. 3 this low yield stress of the base paste does not lead to a yield stress of the syringed material. It is caused by a Theological substructure, which is disturbed by shear stress during releasing out of the cartridge.

EXAMPLES
(all %'s are by weight)

EXAMPLE A
component A
  53.0% dimethylvinyl terminated polydimethylsiloxane containing QM-resins.
  20.0% dimethylvinyl terminated polydimethylsiloxanes containing high disperse $SiO_2$
  5.0% crosslinking H-Silicones (SiH-content 7.5mval/g)
  10.0% chain elongating H-Silicones (SiH-content 2.6 mval/g)
  5.0% zeolith type A
  0.5% titandioxide
  6.5% surfactant (nonylphenoxypolyethylenoxyethanol)
component B
  2:66.5% dimethylvinyl terminated polydimethylsiloxane containing QM-resins.
  32.68% dimethylvinyl terminated olydimethylsiloxanes containing high disperse $SiO_2$
  0.5% Pt-catalyst
  0.05% divinyltetramethyldisiloxane
  0.07% Pt/CaCO3
  0.20% Pigment EXAMPLE B
component A
  53.0% dimethylvinyl terminated polydimethylsiloxane containing QM-resins.
  20.0% dimethylvinyl terminated polydimethylsiloxanes containing high disperse $SiO_2$
  15.0% crosslinking H-Silicones (SiH-content 4.3 mval/g)
  5.0% zeolith type A
  0.5% titandioxide
  6.5% surfactant (nonylphenoxypolyethylenoxyethanol)
component B
  66.5% dimethylvinyl terminated polydimethylsiloxane containing QM-resins.
  32.68% dimethylvinyl terminated polydimethylsiloxanes containing high disperse $SiO_2$
  0.5% Pt-catalyst
  0.05% divinyltetramethyldisiloxane
  0.07W Pt/CaCO3
  0.20W Pigment EXAMPLE C
component A
  16.5% dimethylvinyl terminated polydimethylsiloxanes
  30.0% dimethylvinyl terminated polydimethylsiloxane containing QM-resins.
  20.0% dimethylvinyl terminated polydimethylsiloxanes containing high disperse $SiO_2$
  15.0% crosslinking H-Silicones (SiH-content 4.3 mval/g)
  5.0% zeolith type A
  0.5% titandioxide
  6.0% surfactant (nonylphenoxypolyethylenoxyethanol)
  6.5% hydrophilic modifier (Fa. Wacker)
component B
  36.1% dimethylvinyl terminated polydimethylsiloxanes
  30.0% dimethylvinyl terminated polydimethylsiloxane containing QM-resins.
  32.68% dimethylvinyl terminated polydimethylsiloxanes containing high disperse $SiO_2$
  0.5% Pt-catalyst
  0.4% short chained dimethylvinyl terminated polydimethyl-(vinylmethyl)-siloxanes
  0.07% Pt/CaCO$_3$
  0.43% Pigment

EXAMPLE D component A
- 33.5% dimethylvinyl terminated polydimethylsiloxanes
- 15.0% dimethylvinyl terminated polydimethylsiloxane containing QM-resins.
- 22.50% dimethylvinyl terminated polydimethylsiloxanes containing high disperse $SiO_2$
- 11.0% crosslinking H-Silicones (SiH-content 7.5 mval/g)
- 6.0% dimethylvinyl terminated dimethyl(methylvinyl)-siloxane copolymers (viscosity 5.0 Pas)
- 5.0% zeolith type A
- 1.0% titandioxide
- 6.0% surfactant (nonylphenoxypolyethylenoxyethanol)
- 0.2% spearmint oil component B
- 54.03% dimethylvinyl terminated polydimethylsiloxanes
- 10.0% dimethylvinyl terminated polydimethylsiloxane containing QM-resins.
- 32.90% dimethylvinyl terminated polydimethylsiloxanes containing high disperse $SiO_2$
- 1.0% Pt-catalyst
- 0.10% divinyltetramethyldisiloxane
- 1.0% dimethylvinyl terminated dimethyl(methylvinyl)-siloxane copolymers (viscosity 0.2 Pas)
- 0.07% Pt/CaCO3
- 0.40% Pigment

EXAMPLE E component A
- 44.6% dimethylvinyl terminated polydimethylsiloxanes
- 10.0% dimethylvinyl terminated polydimethylsiloxane containing QM-resins.
- 20.0% dimethylvinyl terminated polydimethylsiloxanes containing high disperse $SiO_2$
- 15.0% crosslinking H-Silicones (SiH-content 4.3 mval/g)
- 5.0% zeolith type A
- 0.2% titandioxide
- 5.0% surfactant (nonylphenoxypolyethylenoxyethanol)
- 0.2% spearmint oil component B
- 57.25% dimethylvinyl terminated polydimethylsiloxanes
- 10.0% dimethylvinyl terminated polydimethylsiloxane containing methylsilesquisiloxane resins. 32.00% dimethylvinyl terminated polydimethylsiloxanes containing high disperse $SiO_2$
- 0.4% Pt-catalyst
- 0.03% divinyltetramethyldisiloxane
- 0.07% Pt/$CaCO_3$
- 0.25% Pigment

EXAMPLE F component A
- 39.1% dimethylvinyl terminated polydimethylsiloxanes
- 10.0% dimethylvinyl terminated polydimethylsiloxanes containing high disperse $SiO_2$
- 8.4% W crosslinking H-Silicones (SiH-content 4.3 mval/g)
- 5.0% calcium sulphate hemihydrate
- 7.0% diatomaceous earth
- 25.0% quartz powder
- 0.2% titandioxide
- 0.2% spearmint oil
- 0.11% pigment
- 5.0% surfactant (nonylphenoxypolyethylenoxyethanol)

component B
- 51.0% dimethylvinyl terminated polydimethylsiloxanes.
- 10.0% dimethylvinyl terminated polydimethylsiloxanes containing high disperse $SiO_2$
- 7.0% diatomaceous earth
- 29.25% quartz powder
- 2.0% plastisizer
- 0.4% Pt-catalyst
- 0.03% divinyltetramethyldisiloxane
- 0.07% Pt/$CaCO_3$
- 1.0% titandioxide Determination of Theological parameters for the examples according to the invention was as follows.

The rheological properties of systems consisting of an insoluble solid filler and two or more non-mixable liquid phases are characterised by rheological substructures as micelles built up by the surfactant and filler particles. The viscosity of these systems especially of emulsions therefore is highly dependent on the shear stress. The viscosity was measured in a creep test with a shear stress of 200 Pa in the case of the single pastes and the mix. The instrument was an Oscillation/Rotation-Rheometer (CS-50 Fa. Bohlin) in a rotation mode. Important for this parameter is that measurement is carried out under constant flow conditions, otherwise the measured value has no physical relevance. The shear stress of 200 Pa is much higher than the yield stress of base pastes according to the invention. Rheological substructures of the pastes are disturbed under these conditions. Under non-destructive conditions the viscosities especially of the base pastes are much higher.

In pastes containing a surfactant (base-pastes) a Theological substructure is built up by the dipolar molecules of the surfactant. At a stress below the yield stress, these micelles together with the filler build up a solid structure. The system behaves quasi-elastically characterised by linear shear-stress/stress-modulus relation. When the shear stress increases the viscosity of the material reaches a maximum and the yield stress is passed over, the substructures are disturbed and the system behaves as a non-Newtonian fluid. The yield stress has been measured with a shear stress slope of 0–100 Pa in a time of 120 seconds. It is noted that this parameter is strongly dependent on the stress/time slope, a steeper slope will result in a lower yield stress. Because of this, the rheological parameters of such systems are usually measured under definite stress situations.

Most often the reorganization of the disturbed substructures is combined with a relaxation time. In such thixotropic systems even the stress history of the system has to be taken into account by the measurement of all Theological parameters. Therefore the material is put on the plate of a cone/plate measuring system 20 minutes (min) before measuring the yield stress. The viscosity is measured in the creep test immediately after putting the material on the measuring system in the case of the single pastes and after a period of 30 sec in the case of the mixed material The setting time $t_c$, is measured in a time sweep on a Rotation/Oscillation-Rheometer (CS-50 Fa. Bohlin) in the oscillation mode. The measurement has to be carried out under non-destructive conditions. These conditions can be realised by measuring inside of the linear viscoelastic range of both the set and unset material. Optimal conditions for the setting reaction of addition curing silicones are a frequency of 1 Hz and a deformation of 0.001. The setting time is read when the shear modulus G*=G'+G" has reached the plateau. The setting time has clinical relevance for the dentist because this period of time is identical with the minimal removal time.

The physical parameters of the examples according to the invention (A, B and D) are shown in Table III together with three examples which are not according to the invention (c, E and F).

TABLE III physical parameters

| Example | Example A | Example B | Example C | Example D | Example E | Example F |
|---|---|---|---|---|---|---|
| viscosity A | 10.4 Pas | 10.1 Pas | 8.18 Pas | 7.37 Pas | 2.39 Pas | 42.2 Pas |
| B | 13.3 Pas | 13.3 Pas | 10.4 Pas | 9.01 Pas | 8.15 Pas | 67.2 Pas |
| mix | 21.2 Pas | 21.1 Pas | | 16.8 Pas | | 76.8 Pas |
| yield stress (base) | 2.13 Pa | | 2.63 Pa | 2.61 Pa | 3.44 Pa | |
| contact angle to water | 42.7° | 38.3° | 44.8° | 43.7° | 40.2° | ca. 45° |
| strain in compression | 8.0% | 6.43% | 7.33% | 5.23% | 6.93% | 3.5–5.0% |
| tear strength | 1.61 MPa | 1.74 MPa | 0.85 MPa | 1.54 MPa | 0.68 | 1.5–3.0 |
| working time (ADA 19) | 106 s | 140 s | 120 s | 104 s | 153 s | 120–150 s |
| compression set (ADA 19) | 0.30% | 0.25% | 0.15% | 0.33% | 0.28% | <0.5% |
| setting time $t_c$ | 300 s | 300 s | 305 s | 325 s | | <300 s |

In formulation F the high tear strength is a result of the high filler content. The viscosities of both the single pastes and the mix are high, therefore the flow characteristics are insufficient to obtain optimal impressions.

In formulation E the low viscosity is obtained by dispensing the filler. The flow characteristic on the tooth surface is very good. The example shows good wetting characteristics as a result of the low contact angle, but because of the very low tear strength the formulation tears off from the undercuts.

In example C the flow characteristics and the contact angle have been optimised, as in formulation E the tear strength is to low to avoid a tear off from the undercuts.

The content of the reinforcing QM-resins is not high enough to improve the mechanical strength.

The examples A, B and D according to the invention have very low viscosities of both the single pastes and the mix. Combined with a low contact angle these rheological characteristics lead to an optimised flow of the paste on the surface of the teeth and into the sulcus. A high tear strength could be achieved by a high network density in the case of example C or by the use of a high content of QM-resins in the case of example A.

TABLE IV shows the gel times $t_g$(unset material) for the base pastes according to the invention measured by a time sweep as explained above.

Together with the gel time the min. viscosity $\eta^*$ after disturbing the Theological structure is important for the flow characteristics of the material. Only in the examples according to the invention (Example A, B and D) a long gel time is combined with a low viscosity.

I claim:

1. A dental impression material having low viscosity comprising from about 45 to about 55 percent by weight based upon 100 percent by weight of the impression material of a base paste comprising:

a1. from about 1 to about 10 percent by weight based upon 100 percent by weight of the impression material base paste of a linear dimethylvinyl terminated polydimethylsiloxane, a2. from about 8 to about 20 percent by weight based upon 100 percent by weight of the impression material base paste of a linear dimethyl-(H-methyl)-siloxane copolymer with a terminated component selected from trimethylsilyl or dimethylhydrosilyl, a3. from about 15 to about 25 percent by weight based upon 100 percent by weight of the impression material base paste of a dimethylvinylsilyl terminated polydimethylsiloxane, wherein said dimethylvinylsilyl terminated polydimethylsiloxane contains 15–25% by weight highly dispersed $SiO_2$ based upon 100% by weight of said dimethylvinylsilyl terminated polydimethylsiloxane, a4. from about 50 to about 60 percent by weight based upon 100 percent by weight of the impression material base paste of a low molecular weight QM-resin, said QM-resin being homogeneously soluble in a1 and comprising $SiO_{4/2}$, $RO_{1/2}$, and $R_3SiO_{1/2}$ wherein R represents n-alkyl, phenyl or vinyl and has an alkoxy group content from less than 4 mmol/g, a5. a water scavenger for adsorption, a6. from about 0 to about 10 percent by weight based upon 100 percent by weight of the impression material base

TABLE IV

| | Example A | Example B | Example C | Example D | Example E | Example F |
|---|---|---|---|---|---|---|
| min. viscosity $\eta^*$ | 39 Pas | 35 Pas | 11 Pas | 45 Pas | 16 Pas | 140 Pas |
| gel time $t_g$(usm) | 101 s | 101 s | * | 30 s | 11 s | 24.5 |

*The base-paste of Example C shows a very long gel time in the time sweep. This formulation has a very week rheological substructure which is disturbed under the measuring conditions (1.0 Hz, 0.0005 radian). It tends to separate under the influence from gravity. Therefore the measurement of the thixotropic effects are without any physical relevance.

paste of a linear dimethyl-(vinylmethyl)-siloxane copolymer with dimethylvinylsilyl termination,
a7. dipolar surfactant to improve wetting properties, and optionally
a8. pigments,
and from about 45 to about 55 percent by weight based upon 100 percent by weight of the impression material of a catalyst paste composition comprising
b1. from about 1 to about 5 percent by weight based upon 100 percent of the catalyst paste of a linear dimethylvinyl terminated polydimethylsiloxane,
b2. from about 30 to about 35 percent by weight based upon 100 percent by weight of the catalyst paste of a dimethylvinylsilyl terminated polydimethylsiloxane, wherein said dimethylvinylsilyl terminated polydimethylsiloxane contains 20–35% highly disperse $SiO_2$ based upon 100% by weight of said dimethylvinylsilyl terminated polydimethylsiloxane,
b3. from about 55 to about 70 percent by weight based upon 100 percent by weight of the catalyst paste of a low molecular weight QM-resin, said QM-resin being homogeneously soluble in a1 and comprising $SiO_{4/2}$, $RO_{1/2}$, and $R_3SiO_{1/2}$ wherein R represents n-alkyl, phenyl or vinyl and has an alkoxy group content from less than 4 mmol/g,
b4. from about 0 to about 10 percent by weight based upon 100 percent by weight of the catalyst paste of a linear dimethyl-(vinylmethyl)-siloxane copolymer with dimethylvinylsilyl termination,
b5. from about 0.5 to about 1.5 percent by weight based upon 100 percent by weight of the catalyst paste of a Pt-catalyst prepared from $H_2PtCl_6$ and tetramethyldivinyldisiloxane
b6. short chained dimethylvinylsilyl terminated polydimethylsiloxanes,
b7. $H_2$-adsorbent, and optionally
b8. pigments.

2. A material according to claim 1 wherein the dimethylvinylsilyl terminated polydimethylsiloxanes has the chemical formula

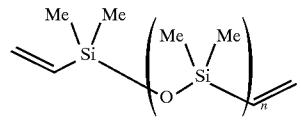

wherein n is an integer of from about 50 to about 1300.

3. A material according to claim 1 having wetting characteristics specified by a contact angle to water below about 45°.

* * * * *